(12) United States Patent
Papautsky et al.

(10) Patent No.: US 9,506,855 B2
(45) Date of Patent: Nov. 29, 2016

(54) METHOD AND SYSTEM FOR ANALYZING A COLORIMETRIC ASSAY

(71) Applicants: University of Cincinnati, Cincinnati, OH (US); The United States of America as Represented by the Secretary of the Air Force, Washington, DC (US)

(72) Inventors: Ian Papautsky, Mason, OH (US); Li Shen, Cincinnati, OH (US); Joshua Hagen, Cincinnati, OH (US); Morley Stone, Spring Valley, OH (US)

(73) Assignee: University Of Cincinnati, Cincinnati, OH (US)

( * ) Notice: Subject to any disclaimer, the term of this patent is extended or adjusted under 35 U.S.C. 154(b) by 8 days.

(21) Appl. No.: 14/376,324

(22) PCT Filed: Feb. 4, 2013

(86) PCT No.: PCT/US2013/024622
§ 371 (c)(1),
(2) Date: Aug. 1, 2014

(87) PCT Pub. No.: WO2013/116831
PCT Pub. Date: Aug. 8, 2013

(65) Prior Publication Data
US 2015/0055134 A1  Feb. 26, 2015

Related U.S. Application Data

(60) Provisional application No. 61/594,683, filed on Feb. 3, 2012.

(51) Int. Cl.
G01N 21/25  (2006.01)
G01J 3/46  (2006.01)
(Continued)

(52) U.S. Cl.
CPC ............. *G01N 21/25* (2013.01); *G01J 3/46* (2013.01); *G01N 21/278* (2013.01); *G01N 21/78* (2013.01);
(Continued)

(58) Field of Classification Search
CPC ....... G01N 21/25; G01N 21/251; G01J 3/46; G01J 3/51; G01J 3/36; G01J 2003/466
USPC .................................. 356/300–425
See application file for complete search history.

(56) References Cited

U.S. PATENT DOCUMENTS 5,850,472 A  12/1998  Alston et al.
6,654,048 B1  11/2003  Barrett-Lennard et al.
(Continued)

OTHER PUBLICATIONS

International Searching Authority, International Search Report and Written Opinion in corresponding Application No. PCT/US2013/024622, mailed Apr. 11, 2013 (9 pages).
(Continued)

*Primary Examiner* — Abdullahi Nur
(74) *Attorney, Agent, or Firm* — Wood Herron & Evans LLP

(57) ABSTRACT

Described herein is a method, system and computer program for analyzing a colorimetric assay that includes obtaining an image of the assay, optionally correcting for ambient lighting conditions in the image, converting the intensity data for at least one of the red channel, the green channel, or the blue channel to a first data point, recalling a predetermined standardized curve, comparing the first data point with the standardized curve, and identifying the value for the assay parameter from the standardized curve.

17 Claims, 13 Drawing Sheets

(51) Int. Cl.
G01N 21/27 (2006.01)
G01N 21/78 (2006.01)
G01N 21/29 (2006.01)

(52) U.S. Cl.
CPC ....... *G01N 21/293* (2013.01); *G01N 2201/061* (2013.01); *G01N 2201/127* (2013.01); *G01N 2201/13* (2013.01)

(56) References Cited

U.S. PATENT DOCUMENTS 7,974,466 B2 7/2011 Pearson et al.
2012/0122123 A1* 5/2012 Boyer .............. G01N 33/56911
435/7.92

OTHER PUBLICATIONS

Garcia, et al., Mobile Phone Platform as Portable Chemical Analyzer, International Journal Devoted to Research and Development of Physical and Chemical Transducers, Apr. 17, 2011, pp. 350-359, vol. 156, No. 1, Elsevier S.A., Switzerland.
Hirayama, et al., Visual and Colorimetric Lithium Ion Sensing Based on Digital Color Analysis, Analytical Chemistry, Feb. 1, 2000, pp. 465-474, vol. 72, No. 3, American Chemical Society, U.S.
Martinez, et al., Simple Telemedicine for Developing Regions: Camera Phones and Paper-Based Microfluidic Devices for Real-Time, Off-Site Diagnosis, Analytical Chemistry, Aug. 15, 2008, pp. 3699-3707, vol. 80, No. 10, American Chemical Society, U.S.
Lee, et al., A Simple and Smart Telemedicine Device for Developing Regions: A Pocket-Sized Colorimetric Reader, Lab on a Chip, Jan. 7, 2011, pp. 120-126, vol. 11, No. 1, Royal Society of Medicine.
Lapresta-Fernandez, et al., Environmental Monitoring Using a Conventional Photographic Digital Camera for Multianalyte Disposable Optica Sensors, Analytica Chimica Acta, Aug. 23, 2011, pp. 328-337, vol. 706, No. 2, Elsevier, Amsterdam, Netherlands.
Loh, N. K., et al., "Automated Mobile pH Reader on a Camera Phone", IAENG International Journal of Computer Science, 38:3, advance online publication Aug. 24, 2011 (pp. 1-7).
A.W. Martinez, S.T. Phillips, M.J. Butte and G.M. Whitesides, AngewandteChemie-International Edition, 2007, 46, 1318-1320.
D.A. Bruzewicz, M. Reches and G.M. Whitesides, Anal. Chem., 2008, 80, 3387-3392.
S. Wang, F. Xu and U. Demirci, Biotechnol. Adv., 2010, 28, 770-781.
M.A. Alyassin, S. Moon, H.0. Keles, F. Manzur, R.L. Lin, E. Haeggstrom, D.R. Kuritzkes and U. Demirci, Lab on a Chip-Miniaturisation for Chemistry and Biology, 2009, 9, 3364-3369.
S. Wang, L. Ge, X. Song, J. Yu, S. Ge, J. Huang and F. Zeng, Biosensors and Bioelectronics, 2012, 31, 212-218.
A.W. Martinez, Bioanalysis, 2011, 3, 2589-2592.
W. Wang, W.-. Wu, W. Wang and J.-. Zhu, Journal of Chromatography A, 2010, 1217, 3896-3899.
D.-. Lee, B.G. Jeon, C. Ihm, J.-. Park and M. Y. Jung, Lab on a Chip-Miniaturisation for Chemistry and Biology, 2011, 11, 120-126.
M.A. Nash, J.M. Hoffman, D.Y. Stevens, A.S. Hoffman, P.S. Stayton and P. Yager, Lab on a Chip-Miniaturisation for Chemistry and Biology, 2010, 10, 2279-2282.
W.G. Lee, Y.-. Kim, B.G. Chung, U. Demirci and A. Khademhosseini, Adv. Drug Deliv. Rev., 2010, 62, 449-457.
P. Yager, T. Edwards, E. Fu, K. Helton, K. Nelson, M.R. Tam and B.H. Weigl, Nature, 2006, 442, 412-418.
A.W. Martinez, S.T. Phillips, G.M. Whitesides and E. Carrilho, Anal. Chem., 2010, 82, 3-10.
L. Yu, C.M. Li, Y. Liu, J Gao, W. Wang and Y. Gan, Lab on a Chip-Miniaturisation for Chemistry and Biology, 2009, 9, 1243-1247.
K. Tohda and M. Gratz!, Analytical Sciences, 2006, 22, 383-388.
K. Suzuki, E. Hirayama, T. Sugiyama, K. Yasuda, H. Okabe and D. Citterio, Anal. Chem., 2002, 74, 5766-5773.
D.J. Soldat, P. Barak and B.J. Lepore, J. Chem. Educ., 2009, 86, 617-620.
E.M.T. Wurm, R. Hofmann-Wellenhof, R. Wurm and H.P. Soyer, JDDG-Journal of the German Society of Dermatology, 2008, 6, 106-112.
V.F. Pamplona, A. Mohan, M. M. Oliveira and R. Raskar, Proceedings of Frontiers in Optics, Adaptive Optics for the Eye (FTuB), 2010,.
S. Wang, X. Zhao, I. Khimji, R. Akbas, W. Qiu, D. Edwards, D.W. Cramer, B. Ye and U. Demirci, Lab on a chip, 2011, 11, 3411-3418.
A.W. Martinez, S.T. Phillips, E. Carrilho, S.W. Thomas III, H. Sindi and G.M. Whitesides, Anal. Chem., 2008, 80, 3699-3707.
A. Garcia, M.M. Erenas, E.D. Marinetto, C.A. Abad, I. De Orbe-Paya, A.J. Palma and L.F. Capitán-Vallvey, Sensors and Actuators, B: Chemical, 2011, 156, 350-359.
K. Cantrell, M. M. Erenas, I. De Orbe-Payáand L F. Capitán-Vallvey, Anal. Chem., 2010, 82, 531-542.
L. Shen, M. M Ratterman, D. Klotzkin and I. Papautsky, Sens. Actuators B, 2011, 155, 430-435 (DOI:DOI: 10.1016/j.snb.2011.01.001).
C. S. McCamy, H. Marcus and J. G. Davidson, J ApplPhotogrEng, 1976, 2, 95-99.
S. Paciornik, A.V. Yallouz, R.C. Campos and D. Gannerman, Journal of the Brazilian Chemical Society, 2006, 17, 156-161.
M.H. Saad, H.I. Saleh, H. Konbor and M. Ashour, Int. J. Comput. Theory Eng., 2011, 3, 701-706.
B.C. Thompson, P. Schottland, K. Zong and J.R. Reynolds, Chemistry of Materials, 2000, 12, 1563-1571.
C. Arbizzani, M.G. Cerroni and M. Mastragostino, Solar Energy Mater. Solar Cells, 1999, 56, 205-211.
H. Jiang, X. Weng and D. Li, Microfluidics and Nanofluidics, 2011, 10, 941-964.
E. Fu, T. Liang, P. Spicar-Mihalic, J. Houghtaling, S. Ramachandran and P. Yager, Anal. Chem., 2012, 84, 4574-4579.
J.-. Cho, S.-. Han, E.-. Paek, I.-. Cho and S.-. Paek, Anal. Chem., 2006, 78, 793-800.

* cited by examiner

METHOD AND SYSTEM FOR ANALYZING A COLORIMETRIC ASSAY

RELATED APPLICATION

The Present application claims priority to U.S. Ser. No. 61/594,683 filed Feb. 3, 2012, the disclosure of which is hereby incorporated herein by reference in its entirety.

FIELD

The present invention is directed to colorimetric diagnostic assays and, more particularly, to processes for analyzing colorimetric diagnostic assays.

BACKGROUND

Paper microfluidic analytical devices have emerged in recent years, leading to development of a number of inexpensive and quick point-of-care ("POC") analyses, including HIV chips, paper ELISA, and other low-cost colorimetric diagnostic assays. Such paper microfluidic assays are gaining popularity as a simple and fast way of disease screening in resource limited environments. Although the colorimetric results of these assays can be viewed by naked eye, it is difficult to precisely quantify the analyte amount. Promising colorimetric detection results have been demonstrated using video cameras, digital color analyzers, scanners or custom portable readers. A key drawback of all these methods is the need for specialized instrumentation and for image analysis with a computer.

Mobile devices with wireless connectivity to remote computer systems, such as smart phones and tablets, offer attractive alternatives for imaging, analysis, and communication of results in the field. For example, with 6 billion mobile phone subscriptions worldwide, mobile phones are becoming ubiquitous. Indeed, several investigators have already demonstrated the use of phones in mobile phones for on-site diagnosis in dermatology, ophthalmology, and colorimetric diagnostics. However, mobile phones have yet to gain popularity for colorimetric detection due to three key challenges. First, integrated color balancing functions of a conventional mobile phone are optimized for photography in high ambient light, and are not suited for images when accurate quantitative measurements must be performed. Second, lighting conditions during imaging can be difficult to control, especially outside of a controlled environment like a laboratory. Third, analysis of images can be challenging especially when small color changes are present, and red, green, blue intensity ("RGB") values alone are not necessarily sufficient. For these reasons, the use of cameras on mobile devices such as mobile phones and tablets has not yet been fully exploited for POC analyses.

SUMMARY

Described herein are methods, systems, and devices for analyzing colorimetric assays, such as those based on paper test strips. The methods, systems, and devices may be utilized with mobile devices such as a cell phone, a tablet, and portable computer. Moreover, the method may also be utilized with less mobile computer systems, such as a desk top system.

An embodiment of the invention is directed to a method of analyzing a colorimetric assay that includes obtaining an image of the assay, optionally correcting for ambient lighting conditions in the image, converting the RGB intensity data to a first data point, recalling a predetermined standardized curve, comparing the first data point with the standardized curve, and identifying the value for the assay parameter from the standardized curve.

The method can also compensate for differences in lighting conditions when taking images under uncontrolled lighting conditions, such as outside of a laboratory setting. The challenges of using a mobile devices as a portable photodetector can all be addressed, as demonstrated herein using two model paper assays—pH paper and urine glucose test strip. Thus, the methods herein allow for the use of mobile devices as a viable tool for quantitative POC analysis.

BRIEF DESCRIPTION OF THE DRAWINGS

The accompanying drawings, which are incorporated in and constitute a part of this specification, illustrate various embodiments of the invention and, together with a general description of the invention given above and the detailed description of the embodiments given below, serve to explain the embodiments of the invention.

DETAILED DESCRIPTION

Figure 1:
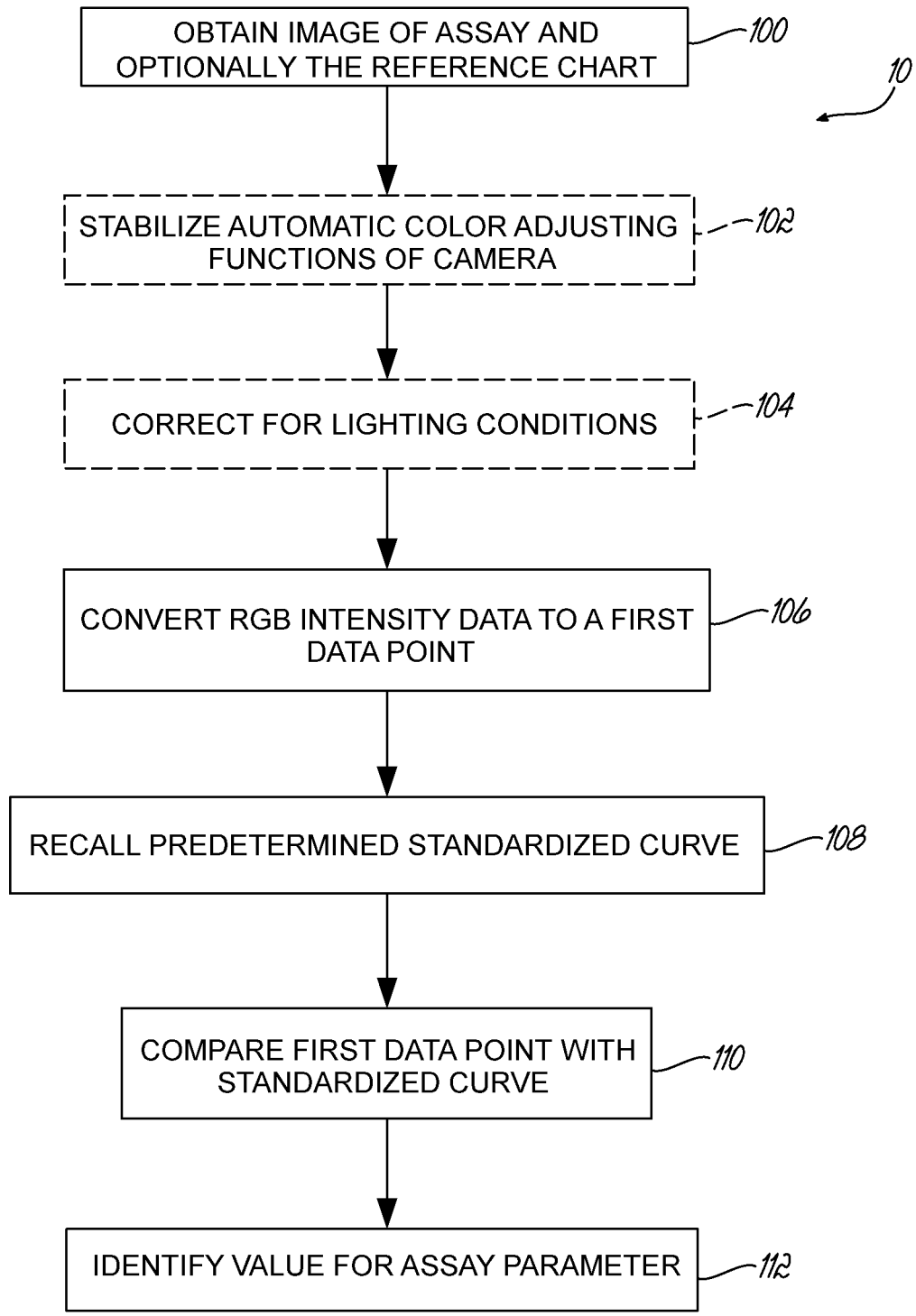
FIG. 1 is a flow chart illustrating the method of analyzing a colorimetric assay in accordance with embodiments of the invention.

With reference to FIG. 1, and in accordance with embodiments of the invention, an improved method 10 of analyzing a colorimetric assay 12 (FIG. 2) to identify the value for an assay parameter (referred to herein as a test assay) that includes obtaining an image of the assay (block 100), optionally stabilizing the automated color correcting functions of the device used to obtain the image (block 102), correcting for ambient lighting conditions in the image (block 104), converting the RGB intensity data to a first data point (block 106), recalling a predetermined standardized curve (block 108), comparing the first data point with the standardized curve (block 110), and identifying the value for the assay parameter from the standardized curve (block 112).

The image may be obtained (block 100) using a device capable of generating a digital image of the test assay. The device includes an electronic sensor capable of capturing the blue, green, and red intensities of the image. Exemplary imaging sensors include charge-coupled device ("CCD") sensors, a complementary metal-oxide-semiconductor ("CMOS") sensor, and a contact image sensor ("CIS").

Figure 2:
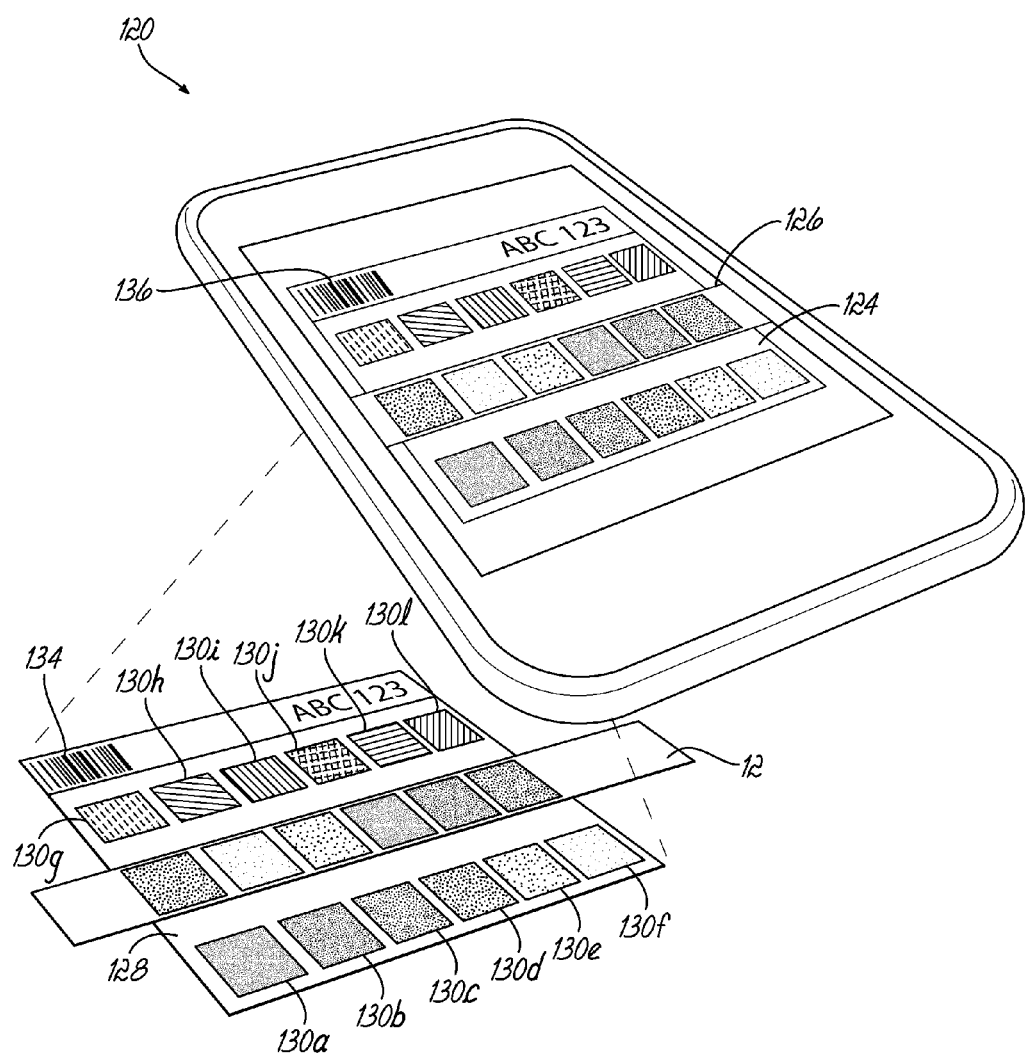
FIG. 2 is a perspective view of a device and system for analyzing a colorimetric assay in accordance with embodiments of the invention.

In an exemplary embodiment, the electronic sensor is included in a device such as a mobile phone, a tablet, a portable computer, a computer, and a scanner. Advantageously, the device is a portable device that also includes processors capable of performing at some of the steps of the methods describes, with preferred portable devices including mobile phone, a tablet, and a portable computer. Other similarly portable devices with similar processing may also be utilized such as devices dedicated to assay analysis. FIG. 2 illustrates an exemplary embodiment wherein the electronic sensor is included in a mobile phone, such as a smart phone 120.

Many mobile phone cameras, such as most smart phone cameras use CMOS arrays, which are low-cost and integrate a range of automated functions, such as Auto White Balance (AWB), designed to provide good color reproduction by adjusting the detected RGB signals at different ratios. The resulting images are brighter and more pleasing to the eyes, making the automatic function popular with non-professional photographers. However, changes in RGB values may skew measurements when attempting to use mobile phone cameras for quantitative measurements. A solution to this challenge is to fully control all camera functions to preserve consistency through the tests. However, this approach may not applicable to mobile phones since these functions are not generally accessible in a fully integrated mobile phone camera. Embodiments of the methods described herein allow for the use of a fully integrated imaging sensor, such as a CMOS sensor or CCD sensor, to accurately analyze a colorimetric assay.

An exemplary embodiment of the method includes optionally obtaining an image of a reference chart 124 simultaneous with obtaining an image of the test assay 126 (FIG. 2). An exemplary reference chart 128 includes 12 reference areas 130a-130l with known color intensities to stabilize the automated color correcting functions of a fully integrated imaging sensor. The exemplary reference chart 128 is also useful in compensating ambient light conditions in the subsequent data processing, as disclosed later. The reference chart 128 is similar to color-rendition charts utilized in photography, in which 24 reference areas are included. The present chart contains seven grayscale regions (130a-130g), and five color regions (130h-130l) that range from short wavelength (blue, 130h) to longer wavelengths (green 130i, yellow 130j, orange 130k, and red 130l). The present reference chart 128 nearly eliminates effects of automatic camera functions, making images reproducible and quantifiable. Skewing the reference chart in the direction of warm colors by including yellow, orange, and red regions overcomes the tendency of AWB to decrease gain in the red channel of the CMOS imaging array, since silicon exhibits better responsiveness at these longer wavelengths. The reduced complexity of the present reference chart 128 compared to the more complex color-rendition charts utilized in photography permit simpler and faster analysis, without sacrificing the quality of the image. Moreover, as disclosed later, the 12-region reference chart is sufficient to build a conversion curve to compensate for differences in ambient light.

The reference chart 128 may be a separate sheet or may be printed directly onto the test assay 12. The reference areas 130a-130l may be arranged in any order on the sheet, such as in one or more rows or in a circular arrangement.

Figure 5:
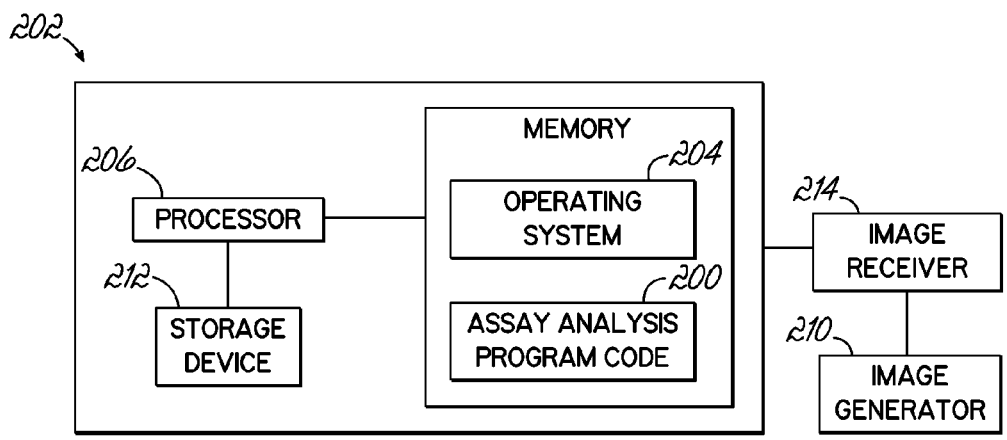
FIG. 5 is a block diagram of a processing system in accordance with embodiments of the invention.

The test assay 12, the reference chart 128, or the combination of the test assay 12 and the reference chart 128 may further include a label portion 134 that includes a machine readable code (illustrated as a barcode) and/or an identifier (illustrated as an alpha numeric code), which may be used for identifying an assay, a protocol, a date, a predetermined standard, and so forth. An image 136 of the machine readable code may be used by the processing system 202 (FIG. 5) to identify and access such information, which may be stored locally on the storage device 212, or retrieved from a resource connected to the processing system 202 via a network. For example, the information may be retrieved from a server.

Figure 3:
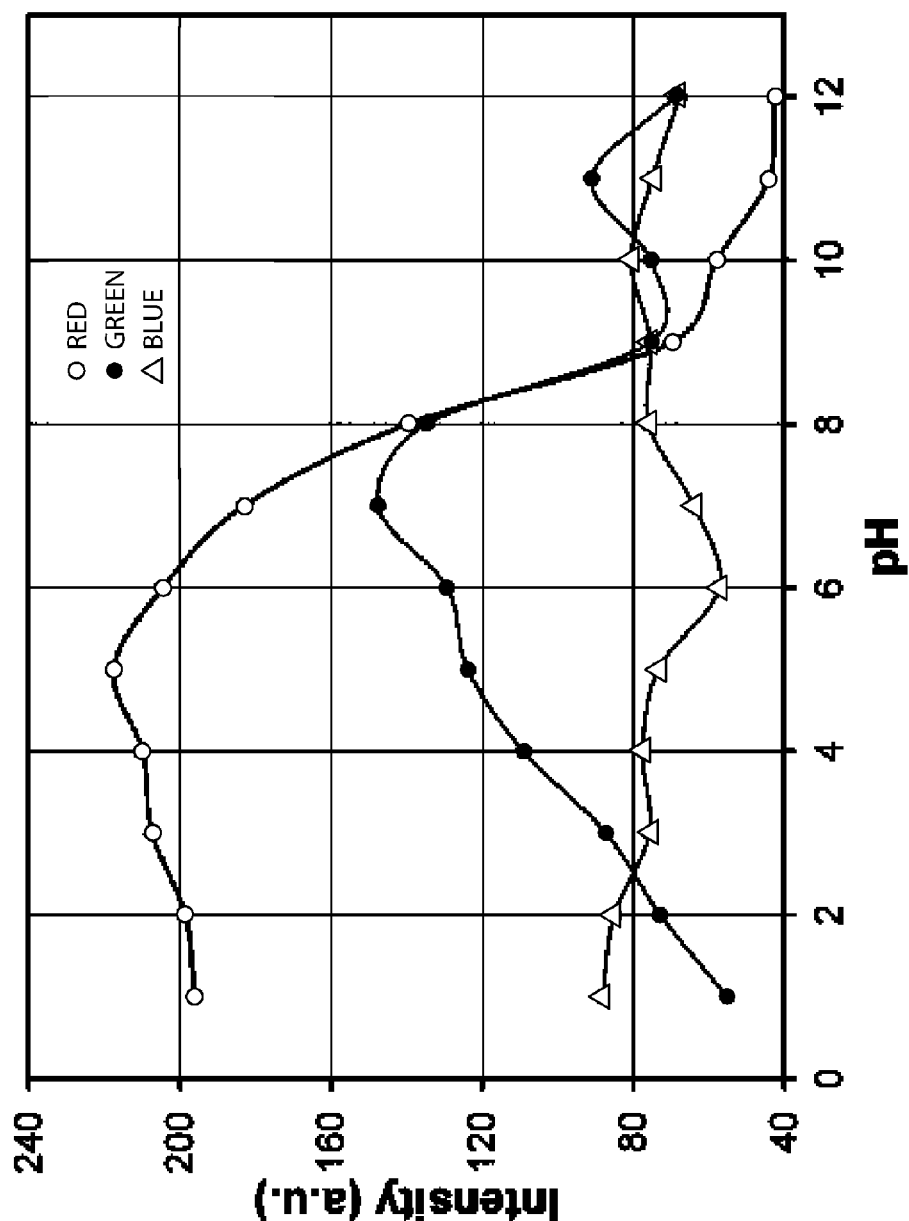
FIG. 3 is a graph illustrating the insufficiency of RGB data in analyzing a colorimetric assay.

While the reference chart assists with accurate colorimetric imaging, the images of the test assay 126 must still be analyzed. The approach of directly converting RGB intensity-values obtained from the image into the corresponding analyte concentrations does not yield useful data. For example, as demonstrated in FIG. 3, a clear illustration of this can be observed from imaging pH paper, which turns colors from red to dark blue according to pH value of the test solution. The RGB values of images for pH increasing from 1 to 12 plotted in FIG. 3 illustrate that RGB intensities do not exhibit any discernible trend and are difficult to correlate with test solution pH values. Prior methods have attempted to address this inadequacy of the direct RGB measurement by using hue values, taking a ratio between red and green channels, or using subtractive CMYK and hue-based HSL values. However, these methods are not sensitive to dark colors and are application specific. The present method overcomes these problems.

Embodiments of the present method convert the intensity data from at least one of the red channel, the green channel, or the blue channel ("RGB") from at least a portion of the image of the first colorimetric assay to a data point having a first value and a second value that indicate the color of the test colorimetric assay (FIG. 1, block 106). In one embodiment, the RGB intensity data is converted to a data point using the CIE color space to code the colorimetric image to overcome inadequacies of the simple RGB analysis. The CIE system is the most recognized method in which color is represented, with tristimulus values X, Y, and Z characterizing the emission color of luminescence data across the wavelength range of visible light. Preferably, the CIE 1931 xyY system is used, in which the Y parameter represents luminance (brightness) of a color and derived parameters x and y determine the chromaticity of a color. Conversion of the obtained image data into the CIE 1931 xyY color space involves three steps, in which the color space terms are derived from the conventional RGB values. In devices that utilize the sRGB color standard, such as digital cameras, cameras in mobile devices such as mobile phones, tablets, and portable computers, the nonlinear sRGB values are converted to linear RGB values using $$C_{linear} = \left(\frac{C_{srgb} + 0.055}{1.055}\right)^{2.4} \quad (1)$$

in which Csrgb stands for Rsrgb, Gsrgb, and Bsrgb, and Clinear indicates Rlinear, Glinear, and Blinear. Then, the linear RGB values can be converted to trisimulus values X, Y, and Z using $$\begin{bmatrix} X \\ Y \\ Z \end{bmatrix} = \begin{bmatrix} 0.4124 & 0.3576 & 0.1805 \\ 0.2126 & 0.7152 & 0.0722 \\ 0.0193 & 0.1192 & 0.9505 \end{bmatrix} \begin{bmatrix} R_{linear} \\ G_{linear} \\ B_{linear} \end{bmatrix} \quad (2)$$

Finally, the chromaticity-values x and y are obtained by $$\begin{cases} x = \dfrac{X}{X+Y+Z} \\ y = \dfrac{Y}{X+Y+Z} \end{cases} \quad (3)$$

The new color space specified by x, y and Y is represented in a 2-D diagram—the Horse Shoe shaped Chromaticity diagram. The pure colors are located on the boundary curve from blue (380 nm) to red (700 nm), while all the mixed colors, such as yellow and pink, are represented within the area enclosed by the curve. The position of a point in the diagram indicates the chromaticity of the corresponding color. In practice, the first and second values of the data point from the colorimetric assay correspond with the x and y coordinates of the image as plotted on the xy chromaticity diagram.

The xy chromaticity diagram of the CIE 1931 system can be used to predict the outcome of a mixture of two colors. The mixed color lies along the straight line connecting the two points of the original colors on the xy chromaticity diagram. The ratio of the two original colors determines the position of the mixed color. This can be potentially useful in more complicated colorimetric assays. Notably, the hue and saturation of a color, based on which the widely used HSV and HSL models were defined, can be derived from its location on the xy diagram. Considering these assets of the CIE 1931 xyY color space, the present method to analyzing colorimetric assays to quantify the colors is versatile and works well as demonstrated in the Examples discussed below.

Figure 6A:
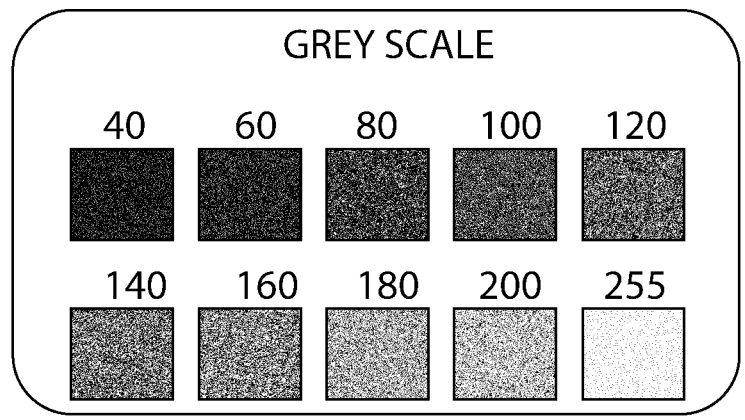
FIG. 6A is a grey scale image for an imaging sensor sensitivity test.
Figure 6B:
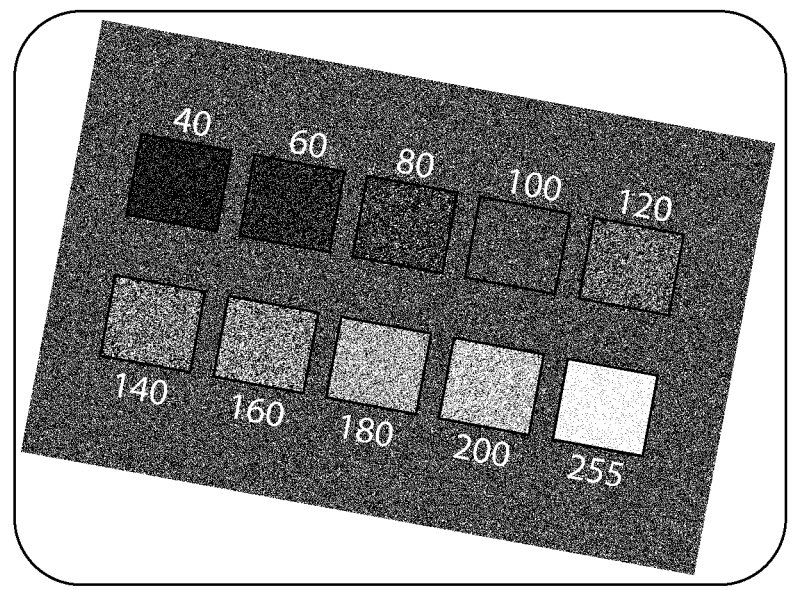
FIG. 6B is a three dimensional surface intensity plot of the grey scale image of FIG. 6A.

The first data point is compared with a predetermined three-dimensional standardized curve. The standardized curve includes a plurality of data points wherein each data point has an x-value, a y-value, and z-value. The x- and y-values correspond with the x and y-values of the xy chromaticity diagram as disclosed above. The z-value corresponds with a predetermined assay-value, such as, for example, an analyte concentration. An exemplary predetermined standardized curves is generated with analytes over a range of known concentrations by obtaining images of a plurality of colorimetric assays conducted with known analyte concentrations, converting the RGB intensity data for each known analyte concentration to a data point having an x-value and a y-value indicative of the chromaticity of the data point and plotting the x-value and the y-value along with the z-value, indicative of the analyte concentration, on a three dimensional curve. The standardized curve includes not only the data points obtained from the assays conducted with known analyte concentrations but also the data points along the curve connecting the data points from the known analyte concentration assays. An exemplary standardized curve is illustrated in FIGS. 5B and 6B, discussed below with reference to the Examples. The standardized curve may be prepared in advance and stored in a storage medium, such as the device's RAM and writable media, from which it is recalled for use in analyzing a test assay (FIG. 1, block 108).

The test assay parameter, such as analyte concentration, is identified by comparing the data point from the test assay with the standardized curve (FIG. 1, blocks 110 and 112). In an embodiment, the test assay parameter is the z-value of a data point along the standardized curve having an x-value and a y-value that most closely matches the x-value and y-value from the data point obtained from the test assay. One method of identifying the data point along the standardized curve that most closely matches the data point from the test assay is to calculate the absolute difference between the data point from the test assay and the data points making up the standardized curve. For example, the difference can be calculated between the x-values and the y-values for the test assay and the standardized curve. The absolute values of the x-value difference and the y-value difference can be summed to identify the absolute difference between the data points. The data point along the standardized curve that most closely matches the data point from the test assay will be the standardized curve data point with the smallest absolute difference from the test assay data point. Other methods for identifying the data point along the standardized curve that most closely matches the test assay data point could also be used.

With reference back to FIG. 1, in some embodiments, the method includes a step for compensating for ambient light conditions (block 104). Variations in ambient light conditions are determined by the position of the light source, light temperature, or outdoor lighting environment. An object absorbs light in a specific wavelength range while reflecting the rest. The CMOS pixel used in many portable devices measures intensity of the reflected light based on many factors, such as the ambient light wavelength, the reflection, the color of the object and the RGB responsivity of the CMOS pixels. A practical way is to treat all these factors as a black box and build a mapping algorithm based on the measured RGB intensities of the references.

Figure 4:
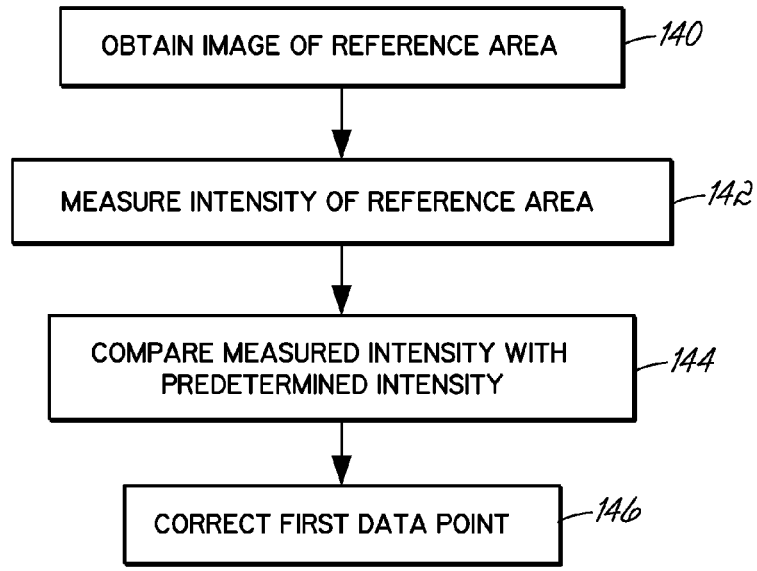
FIG. 4 is a flow chart illustrating the method of compensating for light conditions when analyzing a colorimetric assay in accordance with embodiments of the invention.

With reference to FIG. 4, ambient light compensation includes obtaining an image of a reference chart, such as reference chart 128 (FIG. 2), under the same lighting conditions in which the image of the test assay is obtained (FIG. 4, block 140). For example, the image of the reference chart 128 can be obtained simultaneously with the image of the test assay. The reference chart 128 includes at least one reference area 130a-130l (FIG. 2). In an embodiment, reference charts includes a plurality of areas spanning a range of intensity in both grey scale and color. The intensity of the at least one reference area is measured (block 142). The measured intensity of the at least one reference area is compared with a predetermined intensity of the reference area as measured under a predetermined illumination condition to calculate the ambient light correction required for the test assay data point. The measured intensities of the reference areas a reference chart have a linear relationship between different ambient light conditions. In embodiments measuring the intensity of a plurality of reference areas, an ambient lighting correction curve is plotted with one axis being the measured intensity for each reference area and the other axis being the predetermined intensity for each reference area. The formula defining the resulting curve is then utilized to correct the test assay data point. In an embodiment, the RGB intensity values from the image of the test assay are corrected before being converted to an x-value and a y-value. In another embodiment, the x-value and y-value correction is calculated after conversion.

In some circumstances, the obtained image of the test assay may include areas having different ambient lighting conditions, such as a portion of the image may be in a shadow or exposed to brighter lighting conditions. Embodiments of the invention may recognize and account for changes in lighting conditions across the image. For example, if the measure intensity of one or more reference areas does not have a linear relationship with the remainder of the reference areas, then this would indicate that those references areas are exposed to different ambient lighting conditions. As such, the method could prompt the user to reacquire the image under better lighting conditions or if sufficient data from the reference areas is present, the method could correct the data point associated with the different ambient light condition based on a correction from the nearest reference area. In the alternative, the method could exclude areas wherein the ambient light condition is identified as being different from ambient light condition of the remainder of the image of the test assay.

The methods and systems described herein may be useful for analyzing various types of colorimetric assays so long as the assay results in a colorimetric change that can be detected by the methods described herein. Exemplary assays include pH assays, glucose concentration assays, paper ELISA, and assays that detect proteins, nucleic acids, antibodies, or microorganisms, as well as any assay that can detect the exemplary assay parameter disclosed below. Exemplary assay parameters that may be quantified include an analyte concentration, analyte presence, and analyte activity, such as enzyme activity. Specific exemplary analytes include a hydroxide ion, a hydrogen ion, a carbohydrate, a ketone, an alcohol, a lipid, a peptide, a protein, a nucleic acid, an amino acid, an antibody, a nitrite, a drug, a drug metabolite, a cell, a virus, a metal, such as a nanoparticle of a metal like a gold or silver nanoparticle, a salt, a contaminant, and combinations thereof.

Embodiments of the invention include a program code 200 that includes instructions executable on a processor system 202, such as a mobile phone, a tablet, a portable computer, or computer system, for carrying out the steps of the method. In one embodiment, the program code 200 includes instructions for analyzing a colorimetric assay. Embodiments of the invention, whether implemented as part of an operating system 204, application, component, program code 200, object, module or sequence of instructions executed by one or more processing units 206 are referred to herein as "program code." The program code 200 typically comprises one or more instructions that are resident at various times in various memory 208 and storage devices 212 in the processor system 202 that, when read and executed by one or more processors 206 thereof cause that processor system 202 to perform the steps necessary to execute the instructions embodied in the program code 200 embodying the various aspects of the invention.

While embodiments of the invention are described in the context of fully functioning processing systems 202, those skilled in the art will appreciate that the various embodiments of the invention are capable of being distributed as a program product on a computer readable storage medium. The program product may embody a variety of forms. The invention applies equally regardless of the particular type of computer readable storage medium used to actually carry out the distribution of the program code 200. Examples of appropriate computer readable storage media for the program product include, but are not limited to, non-transitory recordable type media such as volatile and nonvolatile memory devices, floppy and other removable disks, hard disk drives, USB drives, optical disks (e.g. CD-ROM's, DVD's, Blu-Ray discs, etc.), among others.

Any of the individual processes described above or illustrated in the figures may be formed into routines, procedures, methods, modules, objects, and the like, as is well known in the art. It should be appreciated that embodiments of the invention are not limited to the specific organization and allocation of program functionality described herein.

In addition, the systems for analyzing the test assays may further include a module for generating an image of the test assay (i.e. a image generator) 210 and a module for receiving the image 214. The image generator may include a device having an imaging sensor such as a CCD sensor, a CMOS sensor, and a CIS. Image generators as known in the art may be used in accordance with the invention. The image receiving module includes components and/or program code to receive an image from the image generator module.

EXAMPLE 1

Figure 6C:
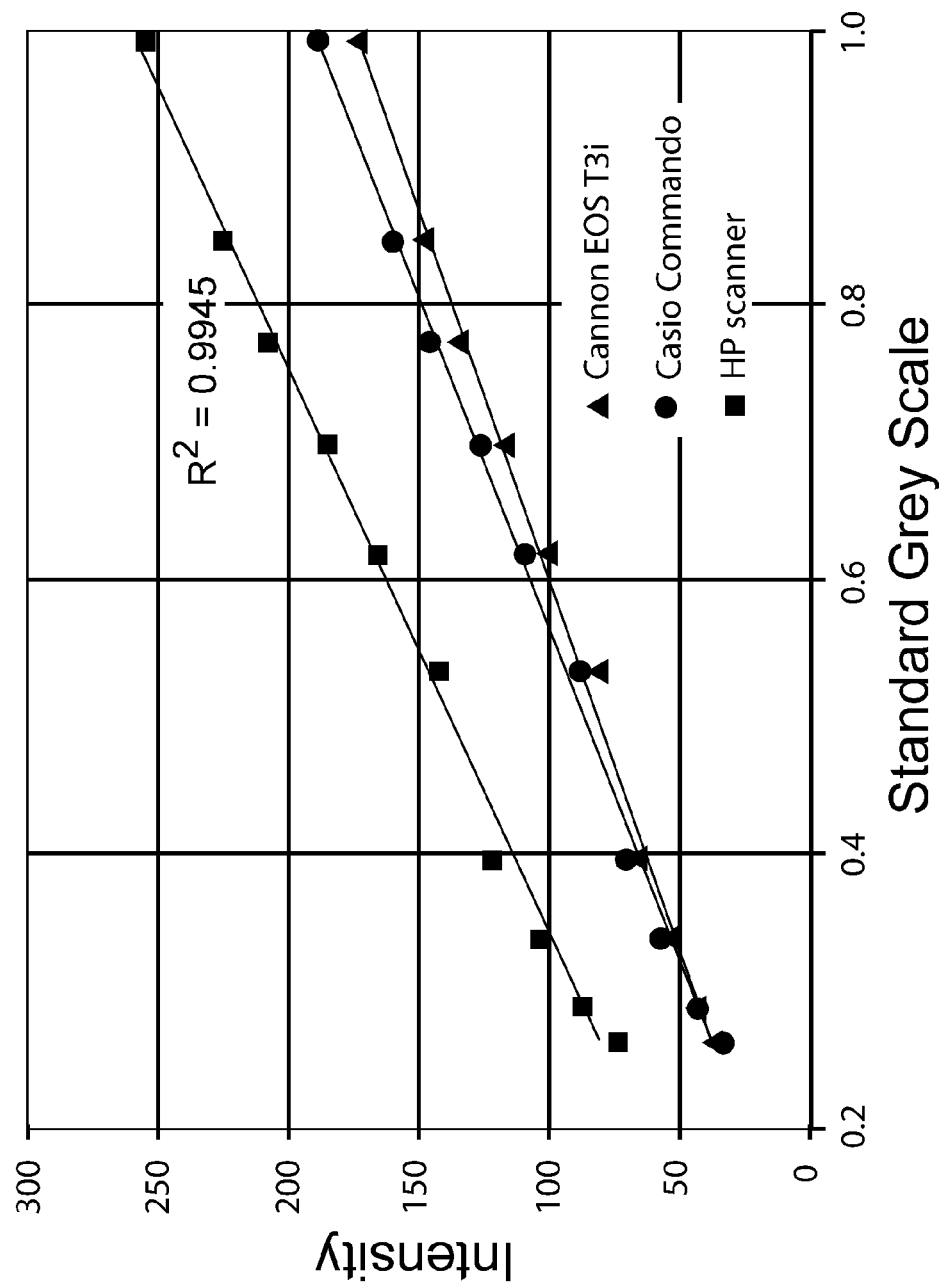
FIG. 6C is a graph illustrating the grey scale sensitivity of multiple imaging sensors.

A smart phone was utilized to examine its suitability as a photodetector and to compare its light sensitivity with other more expensive detectors. The smart phone utilized for this example was the Casio G'zone Commando smartphone, which runs the Android operating system and is ruggedized to military standard MIL-STD-810G. Thus, this phone is stronger and more durable than normal consumer electronics, and is able to handle drops, spills and dirt that may accompany activities such as those in harsh work environments or outdoors. Images of ten grey scale standards were obtained (Labsphere) and the intensities in each image were compared against the intensities obtained with other devices (intensity I=0 is black while the maximum value I=255 for the Commando's 8-bitcolor depth is white). A flatbed desktop scanner (HP Scanjet N6310, 12-bit color depth) and an SLR camera (Canon EOS T3i, 22-bit color depth) were used for sensitivity comparison. FIGS. 6A, 6B, and 6C, illustrates the mean intensities of the grey scale regions in each image, with all imaging devices showing a linear response. The differences in intensities are due to the reflectance of the paper as the surface absorbs a portion light while reflecting the rest. The light collected by the smart phone and SLR cameras was the reflected component of ambient light, while the scanner used an internal light source that was substantially brighter, yielding higher intensity-values. Overall, these results demonstrated that sensitivity of a smart phone camera was comparable to a SLR camera or a desktop scanner when sufficient ambient light was present. The Casio smart phone was used in the following examples to demonstrate the accuracy of the present method in accurately analyzing colorimetric assays.

EXAMPLE 2

Figure 7A:
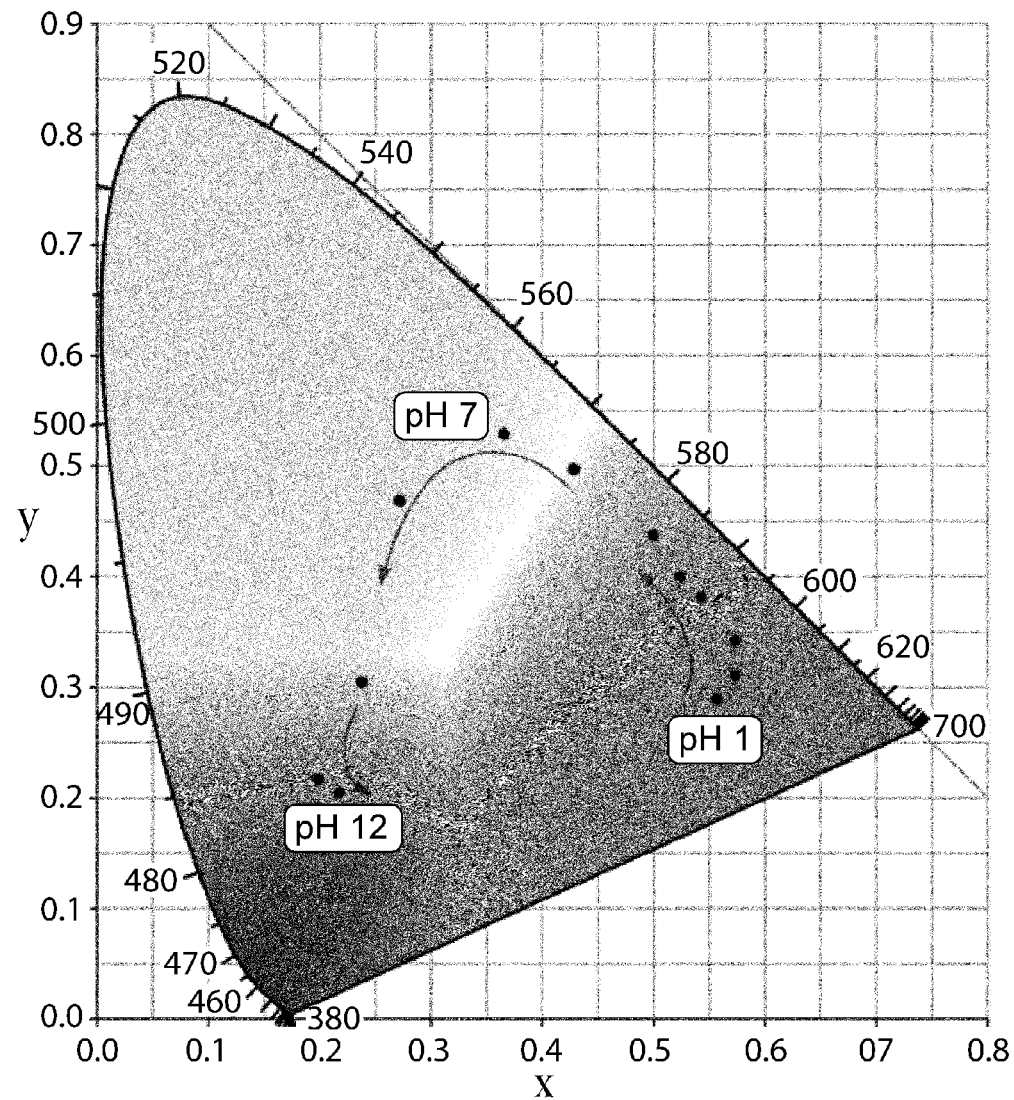
FIG. 7A is a CIE-1931 color map with pH values mapped to the color space in accordance with embodiments of the invention.
Figure 7B:
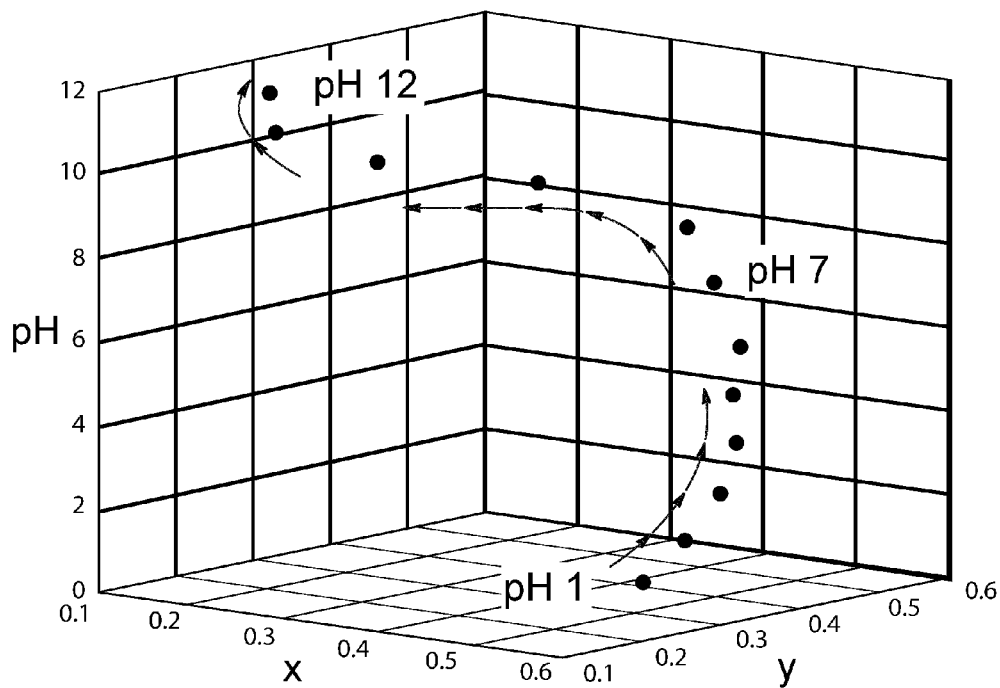
FIG. 7B is a three dimensional plot of the color map from FIG. 7A in accordance with embodiments of the invention.

The described color quantification method can be applied to commercially available colorimetric test strips. The method was demonstrated using colorimetric pH indicator strips (Micro Essential Laboratory) which were dipped into a range of pH buffer solutions and then imaged with the smart phone camera. The mean RGB intensities of the region of interest (ROI) were calculated and converted to the chromaticity-values x and y. FIG. 7A illustrates that the 2-D diagram not only intuitively reflects the color change of the pH strip, but also the corresponding pH change. The pH value appears as a function of the chromaticity-values x and y in the 3-D space (FIG. 6B). A calibration plane was constructed for pH quantification using chromaticity-values of various standard solutions of known pH. The resulting $2^{nd}$ order polynomial equation is given by:

$$pH(x,y)=95.01x^2-0.58y^2+57.94xy-98.71x-21.65y+29.61 \quad (4)$$

Figure 7C:
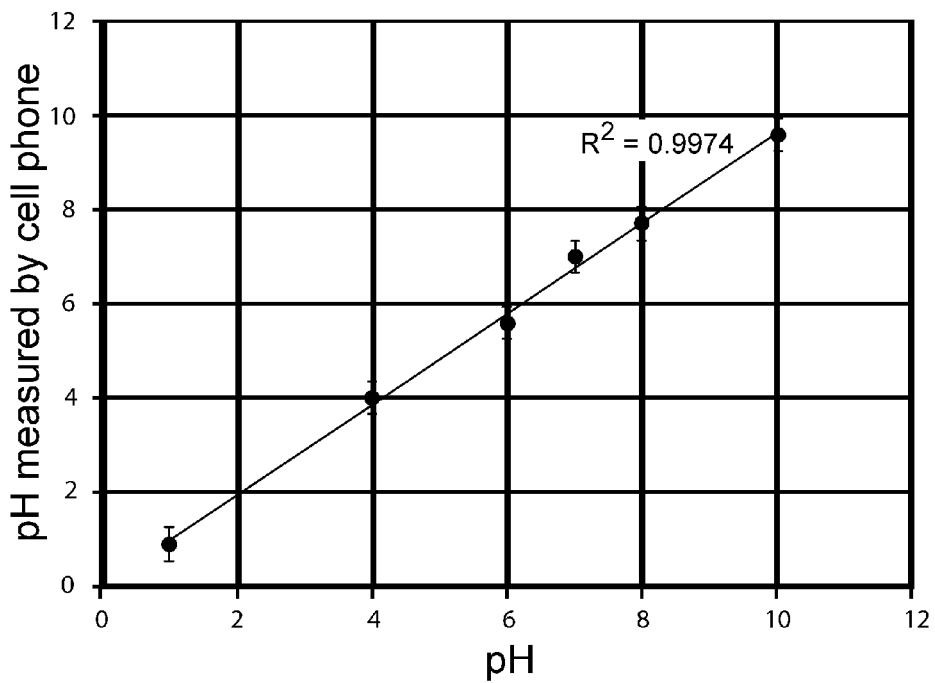
FIG. 7C is a graph demonstrating the correlation between the mapped values from FIG. 7A and the actual pH values from the measured samples.

The high coefficient of determination ($R^2$=0.9874) indicated a highly accurate model. By substituting the x and y-values to the calibrated equation, the corresponding pH value was obtained. FIG. 7C illustrates the standard curve for measuring pH in the range from 2 to 10. The observed sensitivity of ~0.5 is limited by the pH strip, and can be improved by using narrow range pH strips for more accurate measurements.

EXAMPLE 3

Figure 8A:
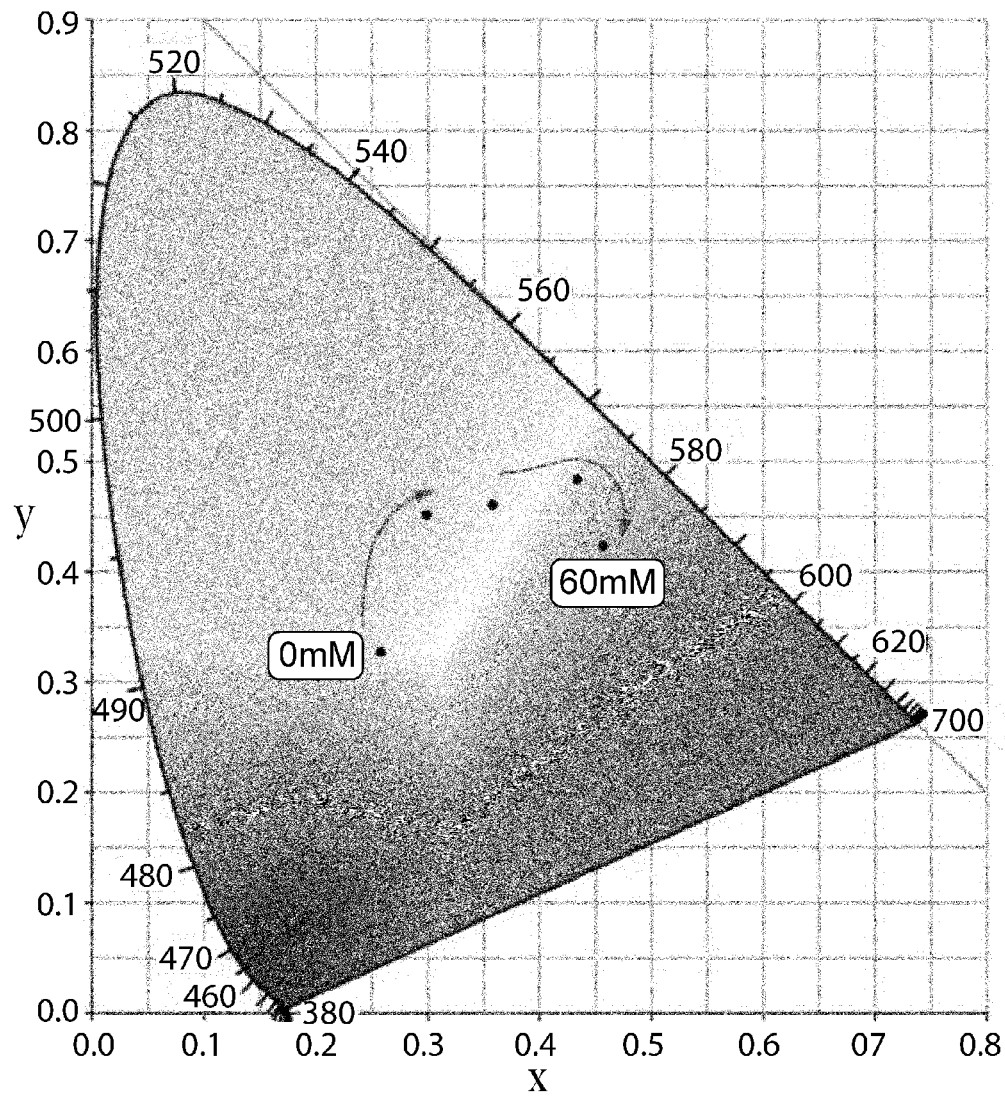
FIG. 8A is a CIE-1931 color map with glucose values from a urine glucose strip mapped to the color space in accordance with embodiments of the invention.
Figure 8B:
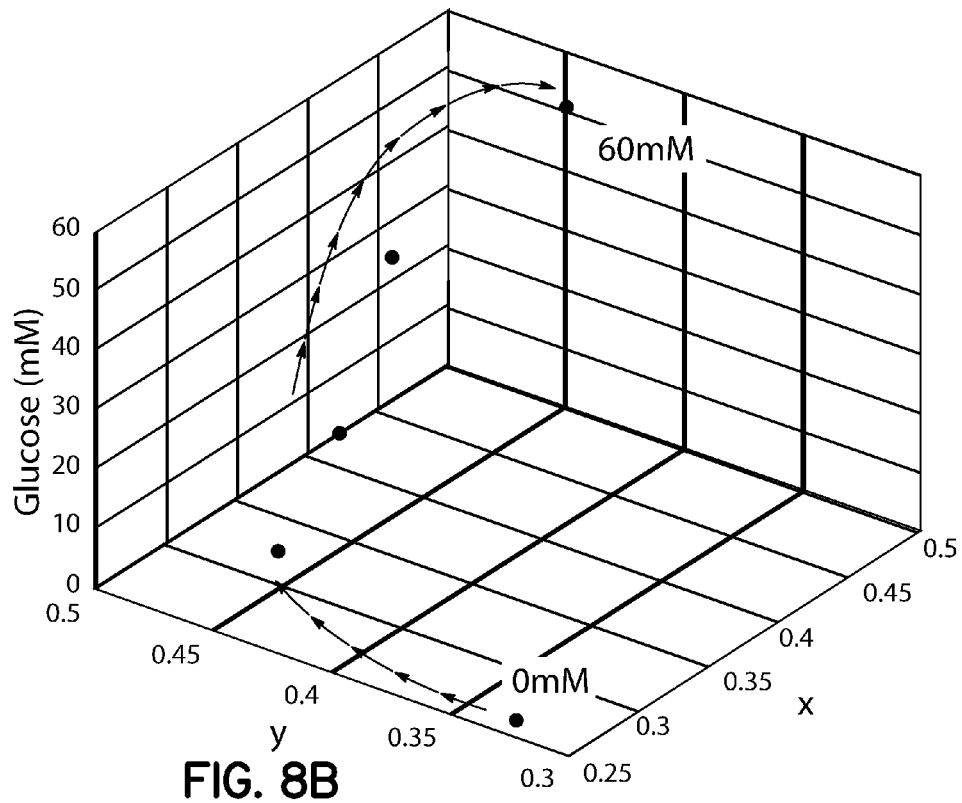
FIG. 8B is a three dimensional plot of the color map from FIG. 8A in accordance with embodiments of the invention.
Figure 8C:
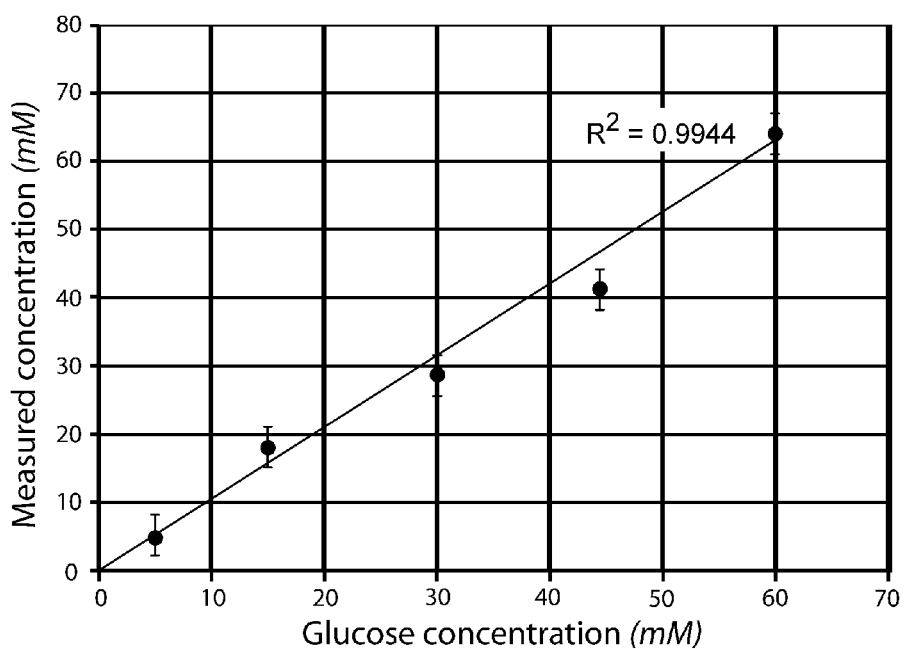
FIG. 8C is a graph demonstrating the correlation between the mapped values from FIG. 8A and the actual values from the measured samples.

A calorimetric urine glucose test strip (Science Kit & Boreal Laboratories) was tested with the method. The calorimetric urine glucose test is a quick and inexpensive way to check glucose in urine and is one of the most commonly used colorimetric tests that can be done in the privacy of one's home or in a doctor's office. The normal glucose range in urine is 0-0.8 mM (0-15 mg/dL); when the glucose level exceeds the renal threshold of ~10 mM, glucose can be found in the urine. The linear range covers the 0-60 mM urine glucose concentration used in clinical diagnostics, and changes color to blue-green when urine glucose concentration exceeds 5 mM. A double sequential enzymatic reaction, involving glucose oxidase and peroxidase in the presence of an indicator is responsible for the color change. To demonstrate test strip operation, urine was spiked with 0-60 mM glucose. FIGS. 8A, 8B, and 8C illustrate the results. After color quantification, the glucose concentration can be expressed as $$c_{glucose}(x,y)=-3181x^2+1803y^2+931.8xy+1005x-571.1y-59.36 \quad (5)$$

The high coefficient of determination ($R^2$=0.9874) once again indicates a highly accurate model. The standard curve for measuring urine glucose in the 0-60 mM range is shown in FIG. 8C. The observed limit of detection of 5 mM is the limitation of the test strip, but is comparable with results of a colorimetric reader with multiple photodetectors.

It is noted that the calibration curves developed for both pH and urine glucose tests above show dependence on the smart phone CMOS chip. The tests with HTC and BlackBerry phones show slight variations (<5%), indicating necessity of re-calibration for each new smart phone model used if higher precision is desired. Nevertheless, only initial calibration is necessary and the process does not need to be repeated for each measurement. It is also noted that additional measurement errors can be caused by differences in ambient light conditions when test strips are imaged. Thus, the effect of ambient light was examined and an approach for its compensation was developed.

EXAMPLE 4

Figure 9A:
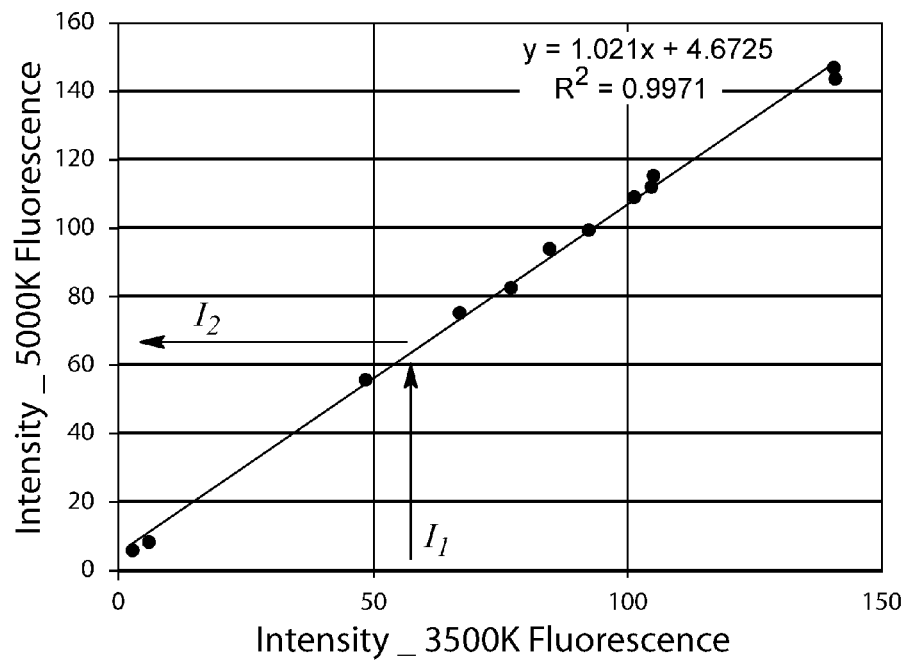
FIG. 9A is a plot demonstrating the linearity between illumination under a standard lighting condition of a 5000 k fluorescent light and an ambient condition of a 3500 k fluorescent light in accordance with embodiments of the invention.
Figure 9B:
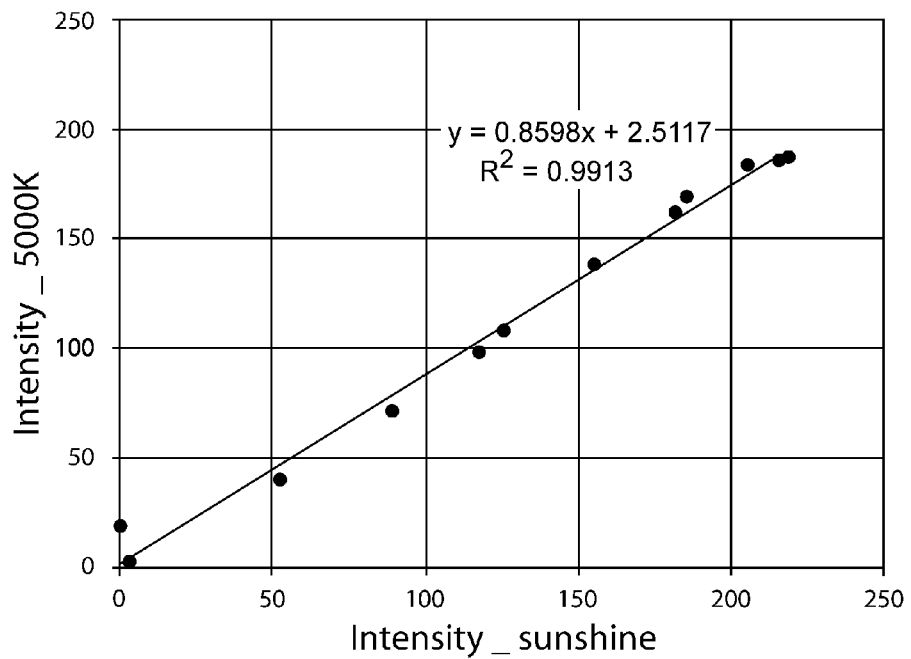
FIG. 9B is a plot demonstrating the linearity between illumination under a standard lighting condition of a 5000 k fluorescent light and an ambient condition of sunshine in accordance with embodiments of the invention.
Figure 9C:
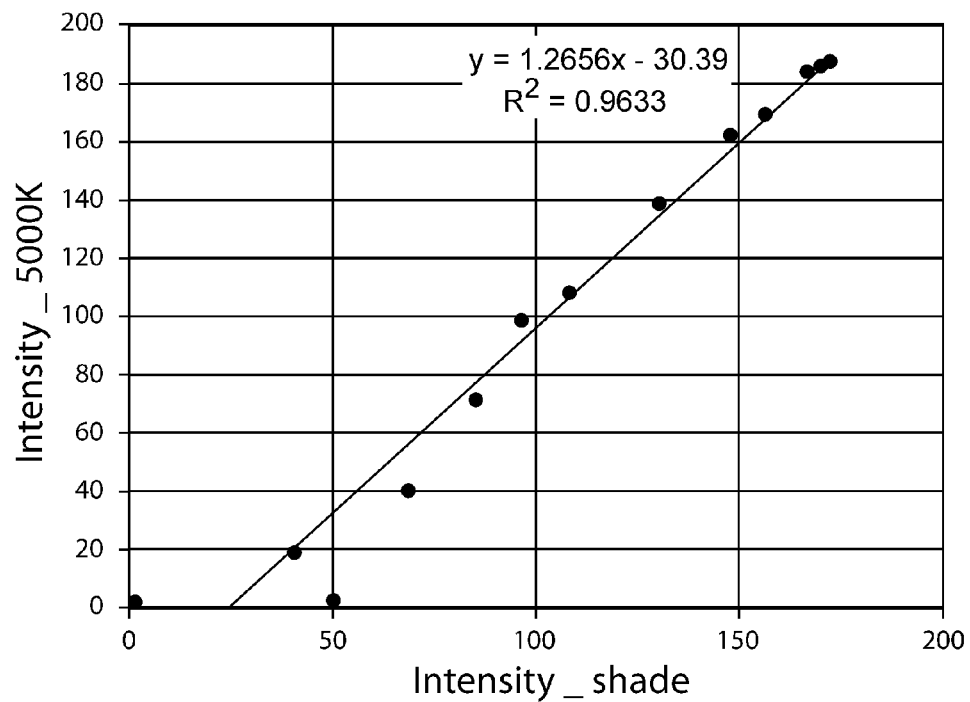
FIG. 9C is a plot demonstrating the linearity between illumination under a standard lighting condition of a 5000 k fluorescent light and an ambient condition of shade in accordance with embodiments of the invention.
Figure 9D:
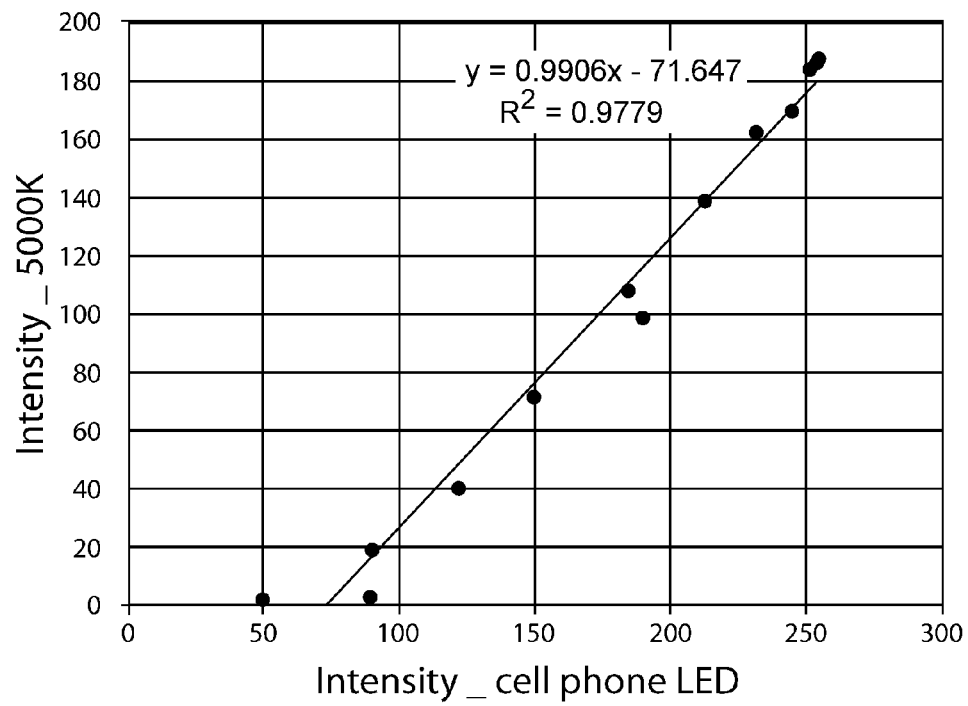
FIG. 9D is a plot demonstrating the linearity between illumination under a standard lighting condition of a 5000 k fluorescent light and an ambient condition of mobile phone LED in accordance with embodiments of the invention.

While the bench top results above demonstrate the capability of using a mobile phone such as a smart phone for quantitative colorimetric analysis, a challenge for everyday use outside of a controlled setting is compensating for ambient light conditions. After measuring the 12 regions on the reference chart, it was found that the measured intensities between different ambient light conditions had a linear relationship. FIGS. 9A, 9B, 9C, and 9D illustrate the red channel intensities of the reference chart regions at 5000K fluorescent light, compared to other light conditions, such as 3500K fluorescence (FIG. 9A), sunshine (FIG. 9B), shade (FIG. 9C), and smart phone LED (FIG. 9D). The high coefficient of determination values ($R^2$>0.99) indicate excellent linearity of the fits, demonstrating that the reference color chart can be used to compensate the intensity differences caused by ambient light changes. As is illustrated in FIG. 9A, the measured intensities at one light condition $I_1$ can be mapped to another $I_2$. The test strips responses and the corresponding 3-D fitting model using a 5000K fluorescent light source were calibrated and the detection tests were run under other light conditions. By building the compensating equations in the red, green, and blue pixel channels, RGB intensities of any imaged sample can be mapped to the 5000K exposure and the corresponding chromaticity-values calculated. This color mapping approach provides an excellent way to compensate for errors caused by the ambient light changes, making the mobile phone detection approach applicable to any lighting environment from indoors to outdoors, from sunshine to overcast.

Figure 10:
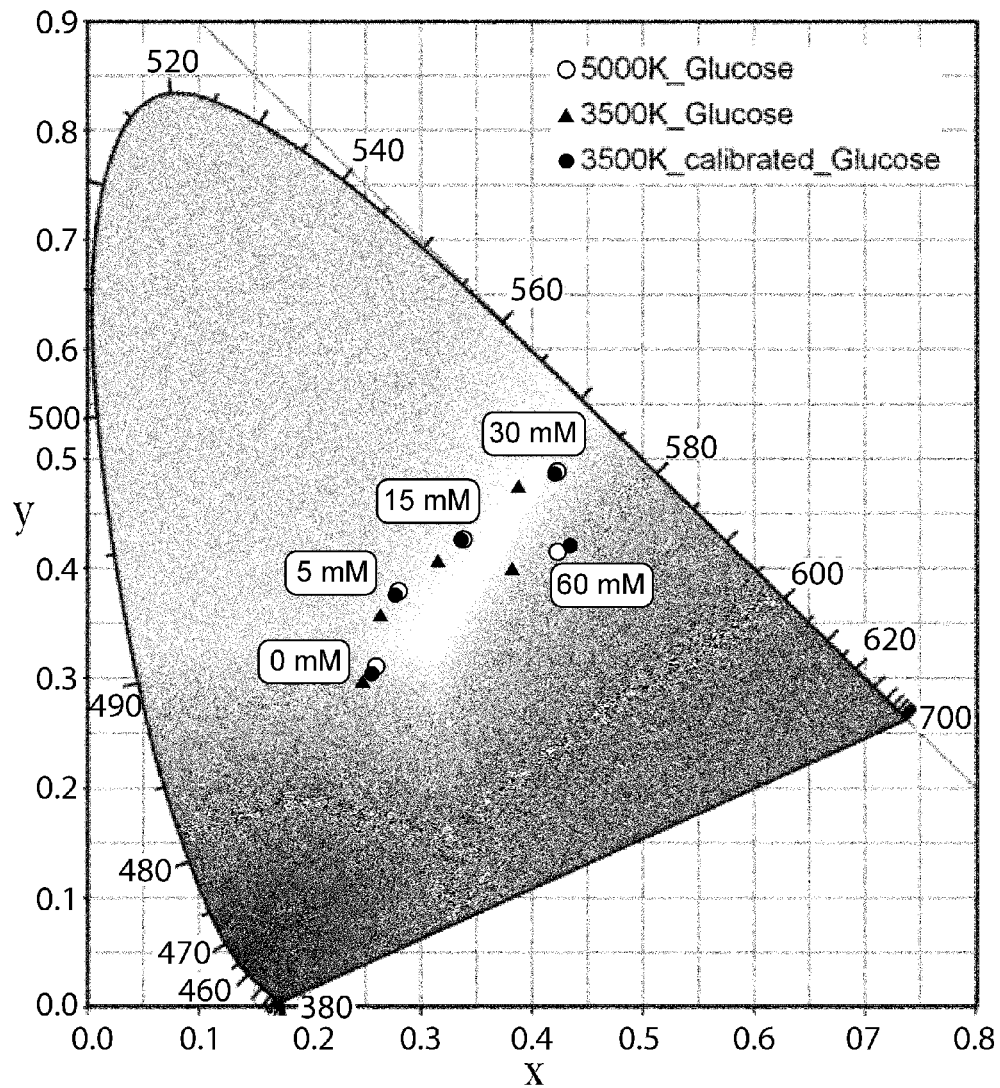
FIG. 10 is a color space map demonstrating a shift of measurements taken under an ambient condition when calibrated against the standard light condition in accordance with embodiments of the invention.

As further proof of the light calibration method, the detection algorithm for urine glucose was calibrated at the 5000K ambient light condition. Then the measurement was repeated at the 3500K ambient light condition. FIG. 10 illustrates the measured chromaticity coordinates of the urine test strips' color response to samples with different glucose concentrations. The chromaticity-values measured under 3500K ambient light exhibit an approximately 0.05 shift in x and 0.03 shift in y which causes large error in glucose detection. After the processing, the different intensities caused by the ambient light were compensated, resulting in a new series of chromaticity coordinates which matches the calibration at 5000K very well. The slight deviation is caused by material of the reference color chart and the test strip paper with different reflection. If the reference chart is printed directly on the test strip, the accuracy of this method can be further improved.

The light compensating method creates mapping of signals detected at any light condition to the calibration light condition, enabling improvisatory calibration of the test. To get an accurate measurement, light sources with high color rendering index are still recommended and the image of the color reference and test strip should be taken with care. The method assumes that the ambient is uniformly shining on the sample so that the intensities of the reference colors can be used to build a precise conversion curve for the unknown sample. If the imaging device is too close to the sample, it may block the light and generate a shadow which breaks the uniformity and causes false measurement. Thus, the smartphone should be placed at a proper position and height, depending on the location of the camera, to get accurate readings.

These data demonstrate the following potential advantages and applications. First, any mobile phone, tablet, portable computer or other device with an imaging sensor can be used for imaging colorimetric tests. According to the International Telecommunication Union (ITU), mobile-cellular subscriptions reached 6 billion in 2011, with 75% in developing countries; a 3-8 megapixel camera is a standard feature for the most of the phones. Using cell phone for imaging colorimetric tests may offer a simple and convenient way to read results (and potentially transmit data to a physician via cellular network). With a smart phone, it may even be possible to process images with the phone for immediate display. Furthermore, using a smart phone for data analysis does not require trained personnel, and can be accomplished in seconds by a novice. Coupled with low-cost paper test strips, smart phones may offer a simple approach to disease screening in developing countries and resource limited settings. It is not expected that smart phone based colorimetric detection will replace traditional microscopic or spectroscopic based diagnostic, but it may offer a low-cost solution for a priori screening of a large number of potential patients.

Second, the approach can be easily extended to images taken by other means. Indeed, the method has been successfully applied it to images obtained by a tablet, a microscope and a scanner. Using Matlab, the color conversion process can be automated for processing on a laptop computer or a tablet (e.g., Fujitsu Q550). The CIE 1931 color system projects all the human visible colors onto a 2-D plane regardless of brightness, and is inherently resistant to changes in intensity in ambient light. The present method is simpler and more accurate than the direct RGB measurement using hue values or ratios of red and green channels. Using color space conversion leads to accurate quantification and ambient light compensation. Further, as already mentioned, with a tablet or mobile phone one could take advantage of cellular network transmission and cloud-based data storage, or perform analysis outside laboratory.

Thirdly, the color conversion analysis technique could be extended beyond imaging colorimetric test strips, and could be applied to analysis of any color images including fluorescence data. The recent development in paper microfluidic immunoassays and ELISA chips make these accurate methods directly accessible to end users, without performing complicated sample handling steps. It is envisioned that the present analysis method will provide a user-friendly approach that matches these assays. Ultimately, it is believed that the methods disclosed herein can be broadly applied to POC diagnosis with any type of colorimetric test strip, or to any sensor systems that provide colorimetric response.

While the present invention has been illustrated by the description of specific embodiments thereof, and while the embodiments have been described in considerable detail, it is not intended to restrict or in any way limit the scope of the appended claims to such detail. The various features discussed herein may be used alone or in any combination. For example, the detailed description primarily discloses analyzing a one test assay from an obtained image, however, multiple test assays could be analyzed in a given image, such as with a paper-based ELISA assay in which multiple areas may be analyzed simultaneously. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of the general inventive concept.

What is claimed is:

1. A method of analyzing a colorimetric assay to identify a value for an assay parameter, the method comprising: obtaining an image of a first colorimetric assay; converting intensity data from at least one of the red channel, the green channel, or the blue channels from at least a portion of the image of the first colorimetric assay to a first data point having a first value and a second value wherein the first value and the second value indicate the chromaticity of the test colorimetric assay; recalling a predetermined standardized curve from a storage medium, the standardized curve including a plurality of data points, each of the plurality of data points having a third value, a fourth value, and a fifth value, the third value and fourth values indicating the chromaticity of the data point along the standardized curve and the fifth value indicating the value of an assay parameter associated with the third value and the fourth value; and comparing the first data point with the standardized curve to identify the value of the assay parameter for the first colorimetric assay, wherein the image is obtained with a device having an imaging sensor selected from the group consisting of a charge-coupled device ("CCD") sensor, a complementary metal-oxide-semiconductor ("CMOS") sensor, and a contact image sensor ("CIS").

2. The method of claim 1 wherein the assay parameter value is identified as the fifth value of the data point along the standardized curve that has a third value and a fourth value that most closely matches the first value and second value of the first data point.

3. The method of claim 2 wherein the most closely matched data point along the standardized curve is identified as the data point having a third value and a fourth value with the smallest absolute difference from the first value and the second value from the first data point.

4. The method of claim 1 wherein the predetermined standardized curve is prepared from a plurality of colorimetric assays having known assay parameter values.

5. The method of claim 1 wherein the predetermined standardized curve is prepared using a device having the same characteristics as the device used to obtain the image of the first colorimetric assay.

6. The method of claim 1 wherein the image is obtained with at least one of a digital camera, a mobile phone, a tablet, a portable computer, a computer, and a scanner.

7. The method of claim 1 wherein the intensity data from the image is converted to a data point using the CIE1931 color space code.

8. The method of claim 1 further comprising:
obtaining an image of a reference chart simultaneously with obtaining the image of the first colorimetric assay, wherein the reference chart includes a plurality of reference areas; and
stabilizing the automated color correcting functions of the device utilized to obtain the image with the reference chart.

9. The method of claim 1 further comprising compensating for the ambient light condition of the image.

10. The method of claim 9 wherein the ambient light compensation step includes:

obtaining an image of a reference chart under the same ambient light conditions as the image of the first colorimetric assay, the reference chart having at least one reference area;

measuring the intensity of the at least one reference area in at least one of the red channel, the green channel, or the blue channel;

comparing the measured intensity of the reference area with a predetermined intensity of the reference area measured under a predetermined illumination condition; and correcting the first and second values of the first data point based on the comparison of the measured intensity of the reference area with the predetermined intensity of the reference area.

11. The method of claim 10 wherein the first data point is corrected by shifting the RGB intensity data from at least one of the red channel, the green channel, or the blue channel from at least a portion of the image of the first colorimetric assay.

12. The method of claim 10 wherein the first data point is corrected by shifting the first value and the second value of the first data point.

13. The method of claim 10 wherein the measured intensity is the measured intensity of at least one of the red channel, the green channel, or the blue channel; and the predetermined intensity is the intensity of at least one of the red channel, the green channel, or the blue channel.

14. A method of compensating for ambient light conditions from an image of a colorimetric assay comprising: obtaining an image of a reference chart under the same ambient light conditions as an image obtained from a colorimetric assay being analyzed, the reference chart having at least one reference area; measuring the intensity of the at least one reference area in at least one of the red channel, the green channel, or the blue channel; comparing the measured intensity of the reference area with a predetermined intensity of the reference area measured under a predetermined illumination condition; and correcting the first and second values of the first data point based on the comparison of the measured intensity of the reference area with the predetermined intensity of the reference area, wherein the image is obtained with a device having an imaging sensor selected from the group consisting of a charge-coupled device ("CCD") sensor, a complementary metal-oxide-semiconductor ("CMOS") sensor, and a contact image sensor ("CIS").

15. A computer program product comprising:

a computer readable storage medium; and program instructions for performing the method of any previous claim, wherein the program instructions are stored on the computer readable storage medium.

16. A system for analyzing a colorimetric assay to identify a value for an assay parameter, the method comprising: an image obtaining module, the image obtaining module configured to receive intensity data points from the colorimetric assay; and a data analysis module, the data analysis module being configured to: a) convert intensity data from at least one of the red channel, the green channel, or the blue channel from at least a portion of an image of a colorimetric assay to a first data point having a first value and a second value wherein the first value and the second value indicate the chromaticity of the test colorimetric assay; b) recall a predetermined standardized curve from a storage medium, the standardized curve including a plurality of data points, each of the plurality of data points having a third value, a fourth value, and a fifth value, the third value and fourth values indicating the chromaticity of the data point along the standardized curve and the fifth value indicating the value of an assay parameter associated with the third value and the fourth value; and c) compare the first data point with the plurality of data points from the standardized curve to identify the value of the assay parameter for the first colorimetric assay.

17. The system of claim 16 further comprising a reference chart, wherein said reference chart includes a plurality of reference areas, the reference chart being configured to stabilize the automated color correcting functions of the image obtaining module.

* * * * *

UNITED STATES PATENT AND TRADEMARK OFFICE
CERTIFICATE OF CORRECTION

Page 1 of 2

PATENT NO. : 9,506,855 B2
APPLICATION NO. : 14/376324
DATED : November 29, 2016
INVENTOR(S) : Ian Papautsky et al.

It is certified that error appears in the above-identified patent and that said Letters Patent is hereby corrected as shown below:

On the Title Page

Column 2, Item (57), Abstract, Line 1, "Described herein is" should read --Described herein are--

Page 2, Column 2, Line 16, citation "Gratz!" should read --Gratzl--

In the Specification

Column 1, Line 4, "The Present" should read --The present--

Column 1, Line 38, "the use of phones in mobile phones" should read --the use of cameras in mobile phones--

Column 2, Line 8, "mobile devices" should read --mobile device--

Column 3, Line 17, "test assay) that includes" should read --test assay) includes--

Column 3, Lines 38-39, "performing at some of the steps of the methods describes" should read --performing at least some of the steps of the methods described--

Column 3, Lines 46-47, "smart phone cameras use" should read --smart phone cameras, use--

Column 3, Lines 57-58, "may not applicable" should read --may not be applicable--

Column 4, Line 20, "permit simpler" should read --permits simpler--

Column 5, Line 25, "trisimulus" should read --tristimulus--

Column 5, Line 64, "method to analyzing" should read --method of analyzing--

Signed and Sealed this
Fifth Day of June, 2018

Andrei Iancu
*Director of the United States Patent and Trademark Office*

CERTIFICATE OF CORRECTION (continued)
U.S. Pat. No. 9,506,855 B2

Column 6, Line 9, "curves is" should read --curve is--

Column 7, Line 4, "charts includes" should read --charts include--

Column 7, Line 12, "areas a reference" should read --areas of a reference--

Column 7, Line 29, "measure intensity" should read --measured intensity--

Column 8, Line 60, "6C, illustrates" should read --6C illustrate--

Column 8, Line 64, "portion light" should read --portion of light--

Column 10, Lines 26-27, "indicate excellence" should read --indicates excellence--

Column 10, Line 66, "ambient is" should read --ambient light is--

Column 11, Line 15, "for the most" should read --for most--

Column 11, Line 15, "Using cell phone" should read --Using a cell phone--

Column 11, Lines 64-65, "analyzing a one" should read --analyzing one--

In the Claims

Claim 2, Column 12, Lines 37-38, "closely matches" should read --closely match--

Claim 16, Column 14, Line 30, "values indicating" should read --value indicating--